US009655672B2

(12) United States Patent
Artale et al.

(10) Patent No.: US 9,655,672 B2
(45) Date of Patent: *May 23, 2017

(54) VESSEL SEALING INSTRUMENT

(75) Inventors: Ryan C. Artale, Boulder, CO (US);
Jeffrey M. Roy, Boulder, CO (US);
Tony Moua, Broomfield, CO (US);
Dennis W. Butcher, Longmont, CO (US);
William J. Dickhans, Longmont, CO (US);
Daniel A. Joseph, Golden, CO (US);
Luke Waaler, Longmont, CO (US);
Cynthia M. Perry, Golden, CO (US);
Meghan Collins Long, Centennial, CO (US)

(73) Assignee: COVIDIEN LP, Mansfield, MA (US)

( * ) Notice: Subject to any disclaimer, the term of this patent is extended or adjusted under 35 U.S.C. 154(b) by 1210 days.

This patent is subject to a terminal disclaimer.

(21) Appl. No.: 12/897,346

(22) Filed: Oct. 4, 2010

(65) Prior Publication Data

US 2012/0083786 A1     Apr. 5, 2012

(51) Int. Cl.
*A61B 18/14*     (2006.01)
*A61B 34/00*     (2016.01)
(Continued)

(52) U.S. Cl.
CPC .......... *A61B 18/1442* (2013.01); *A61B 34/76* (2016.02); *A61B 90/03* (2016.02);
(Continued)

(58) Field of Classification Search
CPC .................. A61B 2018/1455; A61B 2018/146
(Continued)

(56) References Cited

U.S. PATENT DOCUMENTS

| 3,100,489 A | 8/1963 | Bagley |
| D249,549 S | 9/1978 | Pike |

(Continued)

FOREIGN PATENT DOCUMENTS

| CN | 86105764 A | 1/1987 |
| CN | 101507635 A | 8/2009 |

(Continued)

OTHER PUBLICATIONS

U.S. Appl. No. 09/387,883, filed Sep. 119, 1999, Dale F. Schmaltz.
(Continued)

*Primary Examiner* — Thomas Giuliani

(57) ABSTRACT

A bipolar electrosurgical instrument includes first and second shafts each having a jaw member extending from its distal end. Each jaw member is adapted to connect to a source of electrosurgical energy such that the jaw members are capable of selectively conducting energy through tissue held therebetween. A knife channel is configured to reciprocate a cutting mechanism therealong. An actuator selectively advances the cutting mechanism. A switch is disposed on the first shaft and is configured to be depressed between a first position and at least one subsequent position upon biasing engagement with a mechanical interface disposed on the second shaft. The first position of the switch relays information to the user corresponding to a desired pressure on tissue and the at least one subsequent position is configured to activate the source of electrosurgical energy to supply electrosurgical energy to the jaw members.

10 Claims, 8 Drawing Sheets

(51) Int. Cl.
*A61B 90/00* (2016.01)
*A61B 18/00* (2006.01)

(52) U.S. Cl.
CPC ....... *A61B 90/06* (2016.02); *A61B 2018/0063* (2013.01); *A61B 2018/00309* (2013.01); *A61B 2018/00404* (2013.01); *A61B 2018/00601* (2013.01); *A61B 2018/00607* (2013.01); *A61B 2018/00916* (2013.01); *A61B 2018/1412* (2013.01); *A61B 2018/1455* (2013.01); *A61B 2090/034* (2016.02); *A61B 2090/065* (2016.02)

(58) Field of Classification Search
USPC .................................. 606/41, 42, 45, 48–52
See application file for complete search history.

(56) References Cited

U.S. PATENT DOCUMENTS

| | | |
|---|---|---|
| D263,020 S | 2/1982 | Rau, III |
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| 5,122,139 A | 6/1992 | Sutter |
| 5,215,101 A | 6/1993 | Jacobs et al. |
| D343,453 S | 1/1994 | Noda |
| 5,324,289 A | 6/1994 | Eggers et al. |
| D348,930 S | 7/1994 | Olson |
| D349,341 S | 8/1994 | Lichtman et al. |
| D354,564 S | 1/1995 | Medema |
| D358,887 S | 5/1995 | Feinberg |
| 5,443,480 A | 8/1995 | Jacobs et al. |
| 5,472,443 A | 12/1995 | Cordis et al. |
| 5,542,945 A | 8/1996 | Fritzsch |
| D384,413 S | 9/1997 | Zlock et al. |
| 5,797,938 A | 8/1998 | Paraschac et al. |
| 5,833,690 A | 11/1998 | Yates et al. |
| D402,028 S | 12/1998 | Grimm et al. |
| 5,849,022 A | 12/1998 | Sakashita et al. |
| 5,860,976 A | 1/1999 | Billings et al. |
| 5,891,140 A | 4/1999 | Ginn |
| 5,891,142 A | 4/1999 | Eggers et al. |
| 5,911,719 A | 6/1999 | Eggers |
| 5,925,043 A | 7/1999 | Kumar et al. |
| 5,957,923 A | 9/1999 | Hahnen et al. |
| D416,089 S | 11/1999 | Barton et al. |
| 6,010,516 A | 1/2000 | Hulka |
| D424,694 S | 5/2000 | Tetzlaff et al. |
| D425,201 S | 5/2000 | Tetzlaff et al. |
| 6,056,735 A | 5/2000 | Okada |
| 6,059,782 A | 5/2000 | Novak et al. |
| 6,123,701 A | 9/2000 | Nezhat |
| 6,206,877 B1 | 3/2001 | Kese et al. |
| 6,235,027 B1 | 5/2001 | Herzon |
| 6,270,497 B1 | 8/2001 | Sekino et al. |
| D449,886 S | 10/2001 | Tetzlaff et al. |
| D454,951 S | 3/2002 | Bon |
| D457,958 S | 5/2002 | Dycus et al. |
| D457,959 S | 5/2002 | Tetzlaff et al. |
| 6,443,952 B1 | 9/2002 | Mulier et al. |
| D465,281 S | 11/2002 | Lang |
| D466,209 S | 11/2002 | Bon |
| 6,533,778 B2 | 3/2003 | Herzon |
| 6,682,527 B2 | 1/2004 | Strul |
| D493,888 S | 8/2004 | Reschke |
| 6,776,780 B2 | 8/2004 | Mulier et al. |
| D496,997 S | 10/2004 | Dycus et al. |
| 6,802,843 B2 | 10/2004 | Truckai et al. |
| D499,181 S | 11/2004 | Dycus et al. |
| D502,994 S | 3/2005 | Blake, III |
| D509,297 S | 9/2005 | Wells |
| 6,964,662 B2 | 11/2005 | Kidooka |
| D525,361 S | 7/2006 | Hushka |
| 7,083,613 B2 | 8/2006 | Treat |
| 7,083,618 B2 * | 8/2006 | Couture ............ A61B 18/1445 606/49 |
| D531,311 S | 10/2006 | Guerra et al. |
| 7,131,970 B2 | 11/2006 | Moses et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al |
| 7,211,079 B2 | 5/2007 | Treat |
| D545,432 S | 6/2007 | Watanabe |
| D547,154 S | 7/2007 | Lee |
| 7,252,667 B2 | 8/2007 | Moses et al. |
| 7,267,677 B2 | 9/2007 | Johnson et al. |
| 7,329,256 B2 | 2/2008 | Johnson et al. |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| 7,470,272 B2 | 12/2008 | Mulier et al. |
| 7,500,975 B2 | 3/2009 | Cunningham et al. |
| 7,513,898 B2 | 4/2009 | Johnson et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| 7,744,615 B2 | 6/2010 | Couture |
| D621,503 S | 8/2010 | Otten et al. |
| 7,811,283 B2 | 10/2010 | Moses et al. |
| D627,462 S | 11/2010 | Kingsley |
| D628,289 S | 11/2010 | Romero |
| D628,290 S | 11/2010 | Romero |
| D630,324 S | 1/2011 | Reschke |
| 7,887,536 B2 | 2/2011 | Johnson et al. |
| 7,896,878 B2 | 3/2011 | Johnson et al. |
| 7,909,823 B2 | 3/2011 | Moses et al. |
| 7,922,718 B2 | 4/2011 | Moses et al. |
| 8,497,436 B2 | 7/2013 | Palmer et al. |
| 9,345,534 B2 * | 5/2016 | Artale ............... A61B 18/1442 |
| 2002/0188294 A1 | 12/2002 | Couture et al. |
| 2004/0092927 A1 * | 5/2004 | Podhajsky et al. ............ 606/42 |
| 2005/0107784 A1 | 5/2005 | Moses et al. |
| 2005/0119655 A1 * | 6/2005 | Moses ............... A61B 18/1442 606/51 |
| 2005/0154387 A1 | 7/2005 | Moses et al. |
| 2006/0074417 A1 | 4/2006 | Cunningham et al. |
| 2006/0167452 A1 | 7/2006 | Moses et al. |
| 2007/0088356 A1 | 4/2007 | Moses et al. |
| 2007/0106297 A1 | 5/2007 | Dumbauld et al. |
| 2008/0021450 A1 | 1/2008 | Couture |
| 2008/0114356 A1 | 5/2008 | Johnson et al. |
| 2008/0215048 A1 * | 9/2008 | Hafner et al. .................. 606/42 |
| 2008/0319442 A1 | 12/2008 | Unger et al. |
| 2009/0012520 A1 | 1/2009 | Hixson et al. |
| 2009/0138003 A1 | 5/2009 | Deville et al. |
| 2009/0149854 A1 | 6/2009 | Cunningham et al. |
| 2009/0171353 A1 * | 7/2009 | Johnson et al. ................. 606/51 |
| 2009/0240246 A1 * | 9/2009 | Deville et al. .................. 606/33 |
| 2009/0306660 A1 | 12/2009 | Johnson et al. |
| 2010/0023009 A1 | 1/2010 | Moses et al. |
| 2010/0130977 A1 | 5/2010 | Garrison et al. |
| 2010/0204697 A1 | 8/2010 | Dumbauld et al. |
| 2011/0009859 A1 | 1/2011 | Livneh |
| 2011/0034918 A1 | 2/2011 | Reschke |
| 2011/0054472 A1 | 3/2011 | Romero |
| 2011/0077648 A1 | 3/2011 | Lee et al. |
| 2012/0083827 A1 * | 4/2012 | Artale ............... A61B 17/285 606/207 |
| 2012/0172873 A1 * | 7/2012 | Artale et al. ..................... 606/46 |

FOREIGN PATENT DOCUMENTS

| | | |
|---|---|---|
| DE | 2415263 | 10/1975 |
| DE | 2514501 | 10/1976 |
| DE | 2627679 | 1/1977 |

(56) References Cited

FOREIGN PATENT DOCUMENTS

| | | |
|---|---|---|
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 10045375 | 10/2002 |
| DE | 10 2004 026179 | 12/2005 |
| DE | 202007009165 U1 | 8/2007 |
| DE | 20 2007 009317 | 10/2007 |
| DE | 19738457 | 1/2009 |
| EP | 1159926 | 12/2001 |
| EP | 1 532 932 A1 | 5/2005 |
| EP | 1532932 | 5/2005 |
| EP | 1595509 A2 | 11/2005 |
| EP | 1 609 430 A1 | 12/2005 |
| EP | 1 645 240 A2 | 4/2006 |
| EP | 2436327 A1 | 4/2012 |
| JP | 61-501068 | 9/1984 |
| JP | 65-502328 | 3/1992 |
| JP | 5-5106 | 1/1993 |
| JP | 5-40112 | 2/1993 |
| JP | 06343644 | 12/1994 |
| JP | 07265328 | 10/1995 |
| JP | 8-56955 | 5/1996 |
| JP | 08252263 | 10/1996 |
| JP | 09010223 | 1/1997 |
| JP | 10-24051 | 1/1998 |
| JP | 11-070124 | 5/1998 |
| JP | 2000-102545 | 9/1998 |
| JP | 11-169381 | 6/1999 |
| JP | 11244298 | 9/1999 |
| JP | 2000-342599 | 12/2000 |
| JP | 2000-350732 | 12/2000 |
| JP | 2001-008944 | 1/2001 |
| JP | 2001-029356 | 2/2001 |
| JP | 2001-128990 | 5/2001 |
| JP | 2007-188797 | 7/2007 |
| SU | 401367 | 11/1974 |
| WO | WO 00/36986 | 6/2000 |
| WO | 0115614 A1 | 3/2001 |
| WO | WO 01/54604 | 8/2001 |
| WO | WO 2005/110264 | 11/2005 |
| WO | 2010/008663 A1 | 1/2010 |

OTHER PUBLICATIONS

U.S. Appl. No. 09/591,328, filed Jun. 9, 2000, Thomas P. Ryan.
U.S. Appl. No. 12/336,970, filed Dec. 17, 2008, Paul R. Sremeich.
U.S. Appl. No. 12/574,001, filed Oct. 6, 2009, Duane E. Kerr.
U.S. Appl. No. 12/574,292, filed Oct. 6, 2009, Duane E. Kerr.
U.S. Appl. No. 12/576,380, filed Oct. 9, 2009, Wayne Siebrecht.
U.S. Appl. No. 12/607,191, filed Oct. 28, 2009, William H. Nau, Jr.
U.S. Appl. No. 12/619,100, filed Nov. 16, 2009, Jennifer S. Harper.
U.S. Appl. No. 12/692,414, filed Jan. 22, 2010, Peter M. Mueller.
U.S. Appl. No. 12/696,592, filed Jan. 29, 2010, Jennifer S. Harper.
U.S. Appl. No. 12/696,857, filed Jan. 29, 2010, Edward M. Chojin.
U.S. Appl. No. 12/700,856, filed Feb. 5, 2010, James E. Krapohl.
U.S. Appl. No. 12/719,407, filed Mar. 8, 2010, Arlen J. Reschke.
U.S. Appl. No. 12/728,994, filed Mar. 22, 2010, Edward M. Chojin.
U.S. Appl. No. 12/748,028, filed Mar. 26, 2010, Jessica E.C. Olson.
U.S. Appl. No. 12/757,340, filed Apr. 9, 2010, Carine Hoarau.
U.S. Appl. No. 12/758,524, filed Apr. 12, 2010, Duane E. Kerr.
U.S. Appl. No. 12/759,551, filed Apr. 13, 2010, Glenn A. Horner.
U.S. Appl. No. 12/769,444, filed Apr. 28, 2010, Glenn A. Norner.
U.S. Appl. No. 12/770,369, filed Apr. 29, 2010, Glenn A. Horner.
U.S. Appl. No. 12/770,380, filed Apr. 29, 2010, Glenn A. Horner.
U.S. Appl. No. 12/770,387, filed Apr. 29, 2010, Glenn A. Horner.
U.S. Appl. No. 12/773,526, filed May 4, 2010, Duane E. Kerr.
U.S. Appl. No. 12/773,644, filed May 4, 2010, Thomas J. Gerhardt.
U.S. Appl. No. 12/786,589, filed May 25, 2010, Duane E. Kerr.
U.S. Appl. No. 12/791,112, filed Jun. 1, 2010, David M. Garrison.
U.S. Appl. No. 12/792,001, filed Jun. 2, 2010, Duane E. Kerr.
U.S. Appl. No. 12/792,008, filed Jun. 2, 2010, Duane E. Kerr.
U.S. Appl. No. 12/792,019, filed Jun. 2, 2010, Duane E. Kerr.
U.S. Appl. No. 12/792,038, filed Jun. 2, 2010, Glenn A. Horner.
U.S. Appl. No. 12/792,051, filed Jun. 2, 2010, David M. Garrison.
U.S. Appl. No. 12/792,068, filed Jun. 2, 2010, Glenn A. Horner.
U.S. Appl. No. 12/792,097, filed Jun. 2, 2010, Duane E. Kerr.
U.S. Appl. No. 12/792,262, filed Jun. 2, 2010, Jeffrey M. Roy.
U.S. Appl. No. 12/792,299, filed Jun. 2, 2010, Jeffrey M. Roy.
U.S. Appl. No. 12/792,330, filed Jun. 2, 2010, David M. Garrison.
U.S. Appl. No. 12/822,024, filed Jun. 23, 2010, Peter M. Mueller.
U.S. Appl. No. 12/821,253, filed Jun. 23, 2010, Edward M. Chojin.
U.S. Appl. No. 12/832,772, filed Jul. 8, 2010, Gary M. Couture.
U.S. Appl. No. 12/843,384, filed Jul. 26, 2010, David M. Garrison.
U.S. Appl. No. 12/845,203, filed Jul. 28, 2010, Gary M. Couture.
U.S. Appl. No. 12/853,896, filed Aug. 10, 2010, William H. Nau, Jr.
U.S. Appl. No. 12/859,896, filed Aug. 20, 2010, Peter M. Mueller.
U.S. Appl. No. 12/861,198, filed Aug. 23, 2010, James A. Gilbert.
U.S. Appl. No. 12/861,209, filed Aug. 23, 2010, William H. Nau, Jr.
U.S. Appl. No. 12/876,668, filed Sep. 7, 2010, Sara E. Anderson.
U.S. Appl. No. 12/876,680, filed Sep. 7, 2010, Peter M. Mueller.
U.S. Appl. No. 12/876,705, filed Sep. 7, 2010, Kristin D. Johnson.
U.S. Appl. No. 12/876,731, filed Sep. 7, 2010, Kristin D. Johnson.
U.S. Appl. No. 12/877,199, filed Sep. 8, 2010, Arlen J. Reschke.
U.S. Appl. No. 12/877,482, filed Sep. 8, 2010, Gary M. Couture.
U.S. Appl. No. 12/895,020, filed Sep. 30, 2010, Jeffrey M. Roy.
U.S. Appl. No. 12/896,100, filed Oct. 1, 2010, Ryan Artale.
U.S. Appl. No. 12/897,346, filed Oct. 4, 2010, Ryan Artale.
U.S. Appl. No. 12/906,672, filed Oct. 18, 2010, Kathy E. Rooks.
U.S. Appl. No. 12/915,809, filed Oct. 29, 2010, Thomas J. Gerhardt, Jr.
U.S. Appl. No. 12/947,352, filed Nov. 16, 2010, Jason L. Craig.
U.S. Appl. No. 12/947,420, filed Nov. 16, 2010, Jason L. Craig.
U.S. Appl. No. 12/948,081, filed Nov. 17, 2010, Boris Chernov.
U.S. Appl. No. 12/948,144, filed Nov. 17, 2010, Boris Chernov.
U.S. Appl. No. 12/950,505, filed Nov. 19, 2010, David M. Garrison.
U.S. Appl. No. 12/955,010, filed Nov. 29, 2010, Paul R. Romero.
U.S. Appl. No. 12/955,042, filed Nov. 29, 2010, Steven C. Rupp.
U.S. Appl. No. 12/981,771, filed Dec. 30, 2010, James D. Allen, IV.
U.S. Appl. No. 12/981,787, filed Dec. 30, 2010, John R. Twomey.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1965), British Medical Journal Feb. 6, 1976, Vvol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).

(56) References Cited

OTHER PUBLICATIONS

Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique For Determining Dielectric Properties At VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight And Absorbance Imaging Of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04709033.7 dated Dec. 8, 2010.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 004429.2 dated Nov. 2, 2010.

(56) References Cited

OTHER PUBLICATIONS

Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 157500.9 dated Jul. 30, 2010.
Int'l Search Report EP 10 159205.3 dated Jul. 7, 2010.
Int'l Search Report EP 10 160870,1 dated Aug. 9, 2010.
Int'l Search Report EP 10 161596.1 dated Jul. 28, 2010.
Int'l Search Report EP 10 168705.1 dated Oct. 4, 2010.
Int'l Search Report EP 10 169647.4 dated Oct. 29, 2010.
Int'l Search Report EP 10 172005.0 dated Sep. 30, 2010.
Int'l Search Report EP 10 175956.1 dated Nov. 12, 2010.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18674 dated Sep. 18, 2003.
Int'l Search Report PCT/US03/18676 dated Sep. 19, 2003.
Int'l Search Report PCT/US03/28534 dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.
European Search Report for European Application No: 11183476.8 dated Jan. 11, 2012.
International Search Report PCT/US2013/028286 dated Jun. 21, 2013.
Chinese Office Action dated Jul. 25, 2014 issued in Chinese Appln. No. 2011103096356.
Chinese Office Action, and English translation, issued May 20, 2015 in Application No. CN 201110309635.6.
Official Action from Japanese Application No. 2011-219394 dated Jan. 30, 2015.
Extended European Search Report from Appl. No. 13757413.3 dated Sep. 14, 2015.
Chinese Office Action together with the English translation dated Mar. 4, 2016 in corresponding CN Application No. 201380019229.3.
Japanese Office Action together with the English translation dated Mar. 4, 2016 in corresponding JP Application No. 201380019229.3.
Japanese Office Action from Appl. No. 2015-130629 dated May 6, 2016.
Australian Examination Report dated Mar. 2, 2016 in corresponding AU Application No. 2014227486.
Japanese Office Action from Appl. No. 2014-560953 mailed Sep. 28, 2016.
Extended European Search Report from Appl. No. 13182009.4 dated Jun. 16, 2016.
Extended European Search Report from Appl. No. 16157269.8 dated Jun. 16, 2016.
Australian Patent Exam Report from Appl. No. AU 2013230575 issued Oct. 7, 2016.
Chinese Office Action issued in Appl. No. CN 201510390550.3 dated Dec. 20, 2016.

* cited by examiner

VESSEL SEALING INSTRUMENT

BACKGROUND

1. Background of Related Art

The present disclosure relates to forceps used for open surgical procedures. More particularly, the present disclosure relates to a forceps that applies electrosurgical current to seal tissue.

2. Technical Field

A hemostat or forceps is a simple plier-like tool which uses mechanical action between its jaws to constrict vessels and is commonly used in open surgical procedures to grasp, dissect and/or clamp tissue. Electrosurgical forceps utilize both mechanical clamping action and electrical energy to effect hemostasis by heating the tissue and blood vessels to coagulate, cauterize and/or seal tissue.

Certain surgical procedures require sealing and cutting blood vessels or vascular tissue. Several journal articles have disclosed methods for sealing small blood vessels using electrosurgery. An article entitled Studies on Coagulation and the Development of an Automatic Computerized Bipolar Coagulator, J. Neurosurg., Volume 75, July 1991, describes a bipolar coagulator which is used to seal small blood vessels. The article states that it is not possible to safely coagulate arteries with a diameter larger than 2 to 2.5 mm. A second article is entitled Automatically Controlled Bipolar Electrocoagulation—"COA-COMP", Neurosurg. Rev. (1984), pp. 187-190, describes a method for terminating electrosurgical power to the vessel so that charring of the vessel walls can be avoided.

By utilizing an electrosurgical forceps, a surgeon can either cauterize, coagulate/desiccate, reduce or slow bleeding and/or seal vessels by controlling the intensity, frequency and duration of the electrosurgical energy applied to the tissue. Generally, the electrical configuration of electrosurgical forceps can be categorized in two classifications: 1) monopolar electrosurgical forceps; and 2) bipolar electrosurgical forceps.

Monopolar forceps utilize one active electrode associated with the clamping end effector and a remote patient return electrode or pad which is typically attached externally to the patient. When the electrosurgical energy is applied, the energy travels from the active electrode, to the surgical site, through the patient and to the return electrode.

Bipolar electrosurgical forceps utilize two generally opposing electrodes which are disposed on the inner opposing surfaces of the end effectors and which are both electrically coupled to an electrosurgical generator. Each electrode is charged to a different electric potential. Since tissue is a conductor of electrical energy, when the effectors are utilized to grasp tissue therebetween, the electrical energy can be selectively transferred through the tissue.

In order to effect a proper seal with larger vessels, two predominant mechanical parameters must be accurately controlled—the pressure applied to the vessel and the gap between the electrodes both of which affect thickness of the sealed vessel. More particularly, accurate application of the pressure is important to oppose the walls of the vessel, to reduce the tissue impedance to a low enough value that allows enough electrosurgical energy through the tissue, to overcome the forces of expansion during tissue heating and to contribute to the end tissue thickness which is an indication of a good seal. It has been determined that a fused vessel wall is optimum between 0.001 and 0.006 inches. Below this range, the seal may shred or tear and above this range the lumens may not be properly or effectively sealed.

With respect to smaller vessel, the pressure applied to the tissue tends to become less relevant whereas the gap distance between the electrically conductive surfaces becomes more significant for effective sealing. In other words, the chances of the two electrically conductive surfaces touching during activation increases as the vessels become smaller.

Electrosurgical methods may be able to seal larger vessels using an appropriate electrosurgical power curve, coupled with an instrument capable of applying a large closure force to the vessel walls. It is thought that the process of coagulating small vessels is fundamentally different than electrosurgical vessel sealing. For the purposes herein, "coagulation" is defined as a process of desiccating tissue wherein the tissue cells are ruptured and dried and vessel sealing is defined as the process of liquefying the collagen in the tissue so that it reforms into a fused mass. Thus, coagulation of small vessels is sufficient to permanently close them. Larger vessels need to be sealed to assure permanent closure.

Numerous bipolar electrosurgical forceps have been proposed in the past for various open surgical procedures. However, some of these designs may not provide uniformly reproducible pressure to the blood vessel and may result in an ineffective or non-uniform seal. For example, U.S. Pat. No. 2,176,479 to Willis, U.S. Pat. Nos. 4,005,714 and 4,031,898 to Hiltebrandt, U.S. Pat. Nos. 5,827,274, 5,290,287 and 5,312,433 to Boebel et al., U.S. Pat. Nos. 4,370,980, 4,552,143, 5,026,370 and 5,116,332 to Lottick, U.S. Pat. No. 5,443,463 to Stern et al., U.S. Pat. No. 5,484,436 to Eggers et al. and U.S. Pat. No. 5,951,549 to Richardson et al., all relate to electrosurgical instruments for coagulating, cutting and/or sealing vessels or tissue.

Many of these instruments include blade members or shearing members which simply cut tissue in a mechanical and/or electromechanical manner and are relatively ineffective for vessel sealing purposes. Other instruments rely on clamping pressure alone to procure proper sealing thickness and are not designed to take into account gap tolerances and/or parallelism and flatness requirements which are parameters which, if properly controlled, can assure a consistent and effective tissue seal. For example, it is known that it is difficult to adequately control thickness of the resulting sealed tissue by controlling clamping pressure alone for either of two reasons: 1) if too much force is applied, there is a possibility that the two poles will touch and energy will not be transferred through the tissue resulting in an ineffective seal; or 2) if too low a force is applied, a thicker less reliable seal is created.

SUMMARY

According to an embodiment of the present disclosure, a bipolar electrosurgical instrument includes first and second shafts each having a jaw member extending from its distal end and a handle disposed at its proximal end for effecting movement of the jaw members relative to one another about a pivot from a first position wherein the jaw members are disposed in spaced relation relative to one another to a second position wherein the jaw members cooperate to grasp tissue. Each jaw member is adapted to connect to a source of electrosurgical energy such that the jaw members are capable of selectively conducting energy through tissue held therebetween to effect a tissue seal. At least one of the jaw members includes a knife channel defined along its length. The knife channel is configured to reciprocate a cutting mechanism therealong to cut tissue grasped between the jaw members. The instrument also includes an actuator for selectively advancing the cutting mechanism from a first position wherein the cutting mechanism is disposed proximal to tissue grasped between the jaw members to at least one subsequent position wherein the cutting mechanism is disposed distal to tissue grasped between the jaw members. The instrument also includes a switch disposed on the first shaft. The switch is configured to be depressed between a first position and at least one subsequent position upon biasing engagement with a mechanical interface disposed on the second shaft upon movement of the jaw members from the first position to the second position. The first position of the switch relays information to the user corresponding to a desired pressure on tissue grasped between the jaw members and the at least one subsequent position is configured to activate the source of electrosurgical energy to supply electrosurgical energy to the jaw members.

According to another embodiment of the present disclosure, a bipolar electrosurgical instrument includes first and second shafts each having a jaw member extending from its distal end and a handle disposed at its proximal end for effecting movement of the jaw members relative to one another about a pivot from a first position wherein the jaw members are disposed in spaced relation relative to one another to a second position wherein the jaw members cooperate to grasp tissue. Each jaw member is adapted to connect to a source of electrosurgical energy such that the jaw members are capable of selectively conducting energy through tissue held therebetween to effect a tissue seal. A knife channel is defined along a length of one or both of the jaw members. The knife channel is configured to reciprocate a cutting mechanism therealong to cut tissue grasped between the jaw members. The instrument also includes an actuator for selectively advancing the cutting mechanism from a first position wherein the cutting mechanism is disposed proximal to tissue grasped between the jaw members to at least one subsequent position wherein the cutting mechanism is disposed distal to tissue grasped between the jaw members. The instrument also includes a switch disposed on the first shaft. The switch is configured to be depressed between at least two positions upon biasing engagement with the second shaft upon movement of the jaw members from the first position to the second position. The switch generates a first tactile response upon movement to the first position of the switch and a subsequent tactile response upon movement to the at least one subsequent position of the switch. The first tactile response relays information to the user corresponding to a predetermined pressure on tissue grasped between the jaw members and the subsequent tactile response is configured to activate the source of electrosurgical energy to supply electrosurgical energy to the jaw members.

According to another embodiment of the present disclosure, a method of performing an electrosurgical procedure includes the step of approximating first and second shafts of a bipolar forceps to grasp tissue between first and second jaw members associated with the first and second shafts. The method also includes the steps of depressing a switch upon approximation of the first and second shafts to a first position to relay information to the user corresponding to a predetermined grasping pressure applied to tissue grasped between the jaw members and depressing the switch to at least one subsequent position to activate a source of electrosurgical energy to supply electrosurgical energy to the jaw members.

BRIEF DESCRIPTION OF THE DRAWINGS

Various embodiments of the subject instrument are described herein with reference to the drawings wherein.

DETAILED DESCRIPTION

Figure 1:
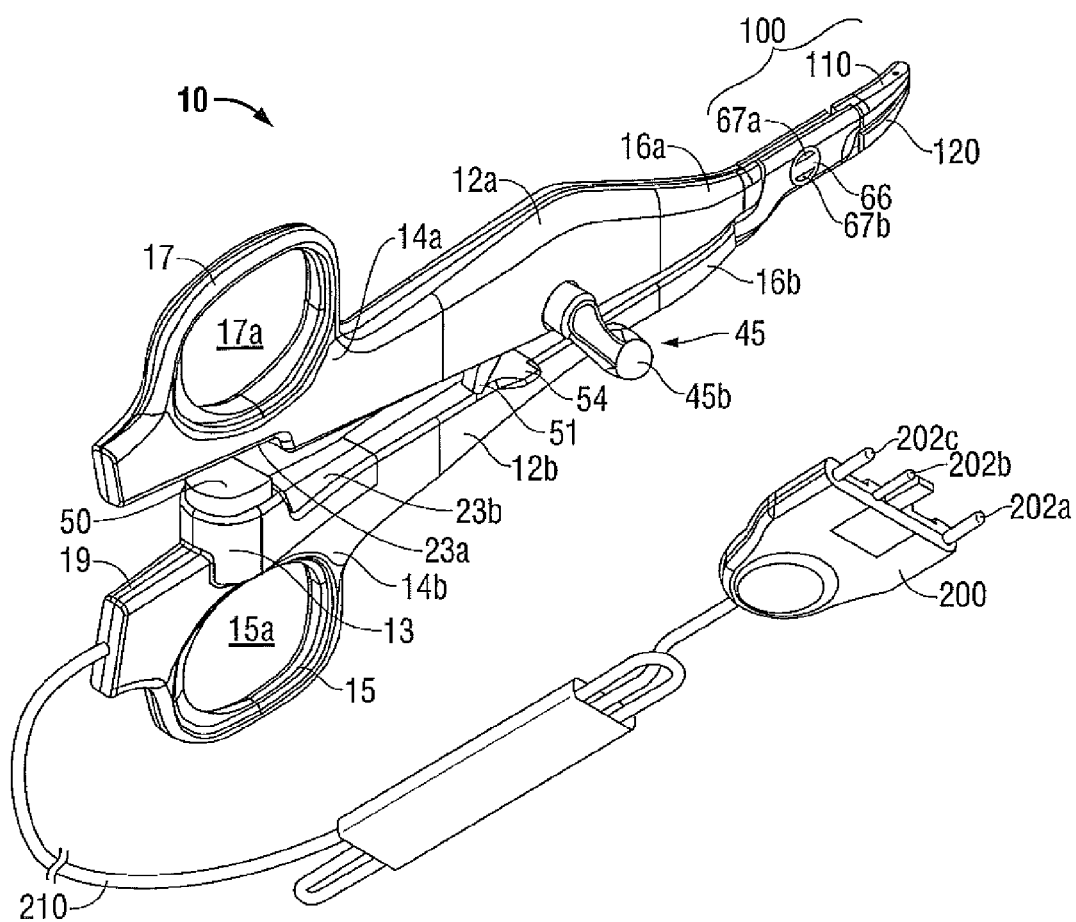
FIG. 1 is a right, perspective view of a forceps according to one embodiment of the present disclosure.
Figure 2:
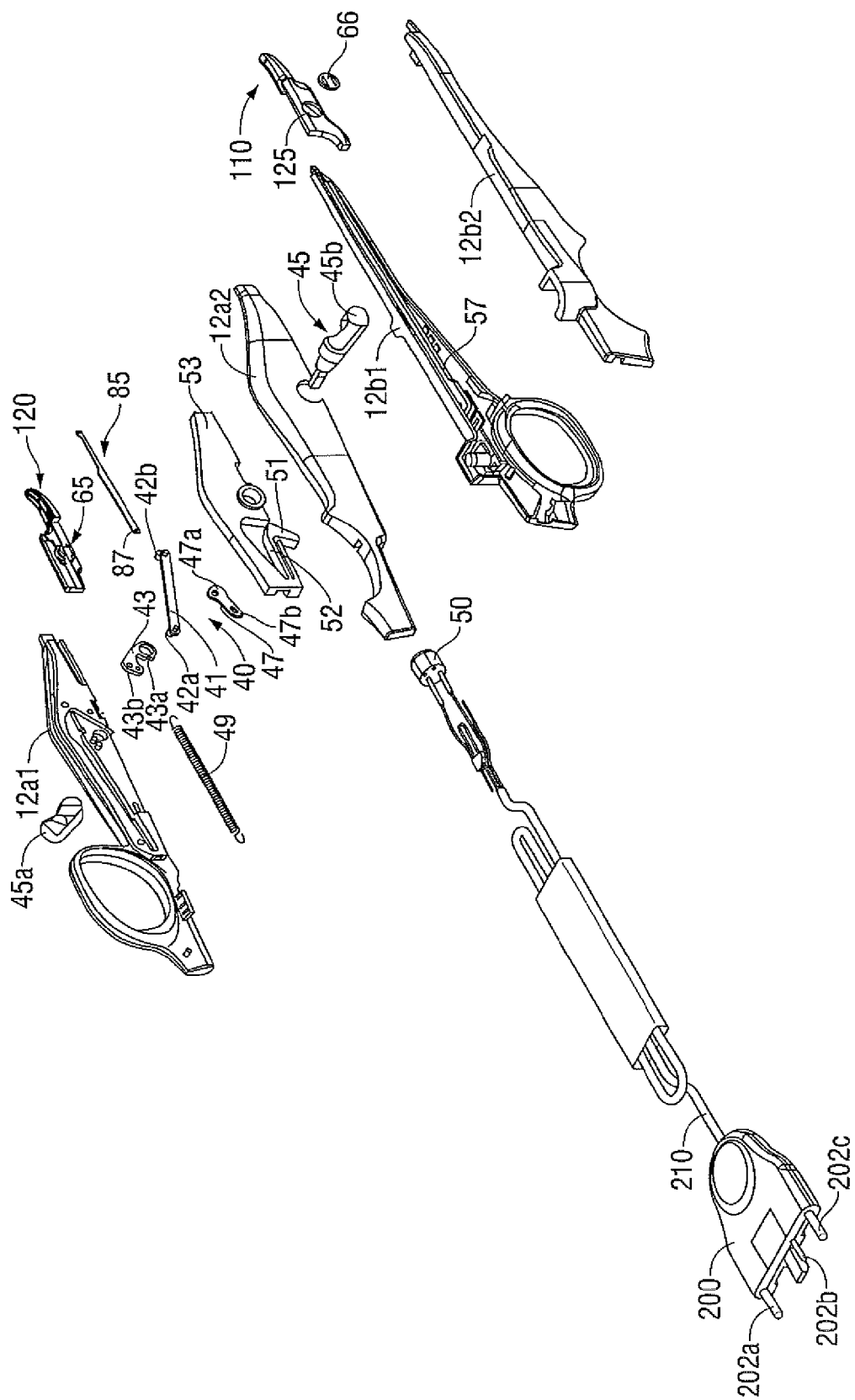
FIG. 2 is an exploded view of the forceps of FIG. 1.

Referring initially to FIGS. 1 and 2, a forceps 10 for use with open surgical procedures includes elongated shaft portions 12a and 12b each having a proximal end 14a, 14b and a distal end 16a and 16b, respectively. In the drawings and in the description that follows, the term "proximal", as is traditional, will refer to the end of the forceps 10 that is closer to the user, while the term "distal" will refer to the end that is further from the user.

The forceps 10 includes an end effector assembly 100 that attaches to the distal ends 16a and 16b of shafts 12a and 12b, respectively. The end effector assembly 100 includes pair of opposing jaw members 110 and 120 that are pivotably connected and movable relative to one another about a pivot 65 (FIG. 2) to grasp tissue. Pivot 65 is disposed on a proximal end of jaw member 120 and includes opposing halves 65a and 65b disposed on opposing sides of a channel 126 (FIG. 4C) that is configured to facilitate reciprocation of a cutting mechanism or knife 85 therethrough (FIG. 2), as discussed in detail below.

Each shaft 12a and 12b includes a handle 15 and 17, respectively, disposed at the proximal end 14a and 14b thereof. Each handle 15 and 17 defines a finger hole 15a and 17a, respectively, therethrough for receiving a finger of the user. Handles 15 and 17 facilitate movement of the shafts 12a and 12b relative to one another which, in turn, pivot the jaw members 110 and 120 from an open position wherein the jaw members 110 and 120 are disposed in spaced relation relative to one another to a clamping or closed position wherein the jaw members 110 and 120 cooperate to grasp tissue therebetween.

As best seen in FIG. 2, shaft 12a is constructed from two components, namely, 12a1 and 12a2, that are coupled together to form shaft 12a. Likewise, shaft 12b is constructed from two components, namely, 12b1 and 12b2, that are coupled together to form shaft 12b. In some embodiments, component halves 12a1 and 12a2 and component halves 12b1 and 12b2 are ultrasonically welded together at a plurality of different weld points and/or may be mechanically coupled together by any suitable method including snap-fitting, adhesive, fastened, etc.

The arrangement of shaft 12b is slightly different from shaft 12a. More particularly, shaft 12a is generally hollow to house the knife 85 and an actuating mechanism 40. The actuating mechanism 40 is operatively associated with a trigger 45 having handle members 45a and 45b disposed on opposing sides of shaft 12a to facilitate left-handed and right-handed operation of trigger 45. Trigger 45 is operatively associated with a series of suitable inter-cooperating elements (e.g., FIG. 2 shows a trigger link 43, a knife pushing link 41, a spring 49, and an anti-deployment link 47) configured to mechanically cooperate (not explicitly shown) to actuate the knife 85 through tissue grasped between jaw members 110 and 120 upon actuation of trigger 45. Handle members 45a and 45b operate in identical fashion such that use of either of handle members 45a and 45b operates the trigger 45 to reciprocate the knife 85 through the knife channel 115 (FIG. 5C). Further, the proximal end 14b of shaft 12b includes a switch cavity 13 protruding from an inner facing surface 23b of shaft 12b and configured to seat a depressible switch 50 therein (and the electrical components associated therewith). Switch 50 aligns with an opposing inner facing surface 23a of the proximal end 14a of shaft 12a such that upon approximation of shafts 12a and 12b toward one another, the switch 50 is depressed into biasing engagement with the opposing inner facing surface 23a of the proximal end 14a of shaft 12a.

As shown in FIG. 1, an electrosurgical cable 210 having a plug 200 at its proximal end connects the forceps 10 to an electrosurgical generator (not shown). More specifically, the distal end of the cable 210 is securely held to the shaft 12b by a proximal shaft connector 19 and the proximal end of the cable 210 includes a plug 200 having prongs 202a, 202b, and 202c that are configured to electrically and mechanically engage the electrosurgical generator.

The tissue grasping portions of the jaw members 110 and 120 are generally symmetrical and include similar component features that cooperate to permit facile rotation about pivot 65 to effect the grasping and sealing of tissue. As a result, and unless otherwise noted, jaw member 110 and the operative features associated therewith are initially described herein in detail and the similar component features with respect to jaw member 120 will be briefly summarized thereafter.

Figure 3A:
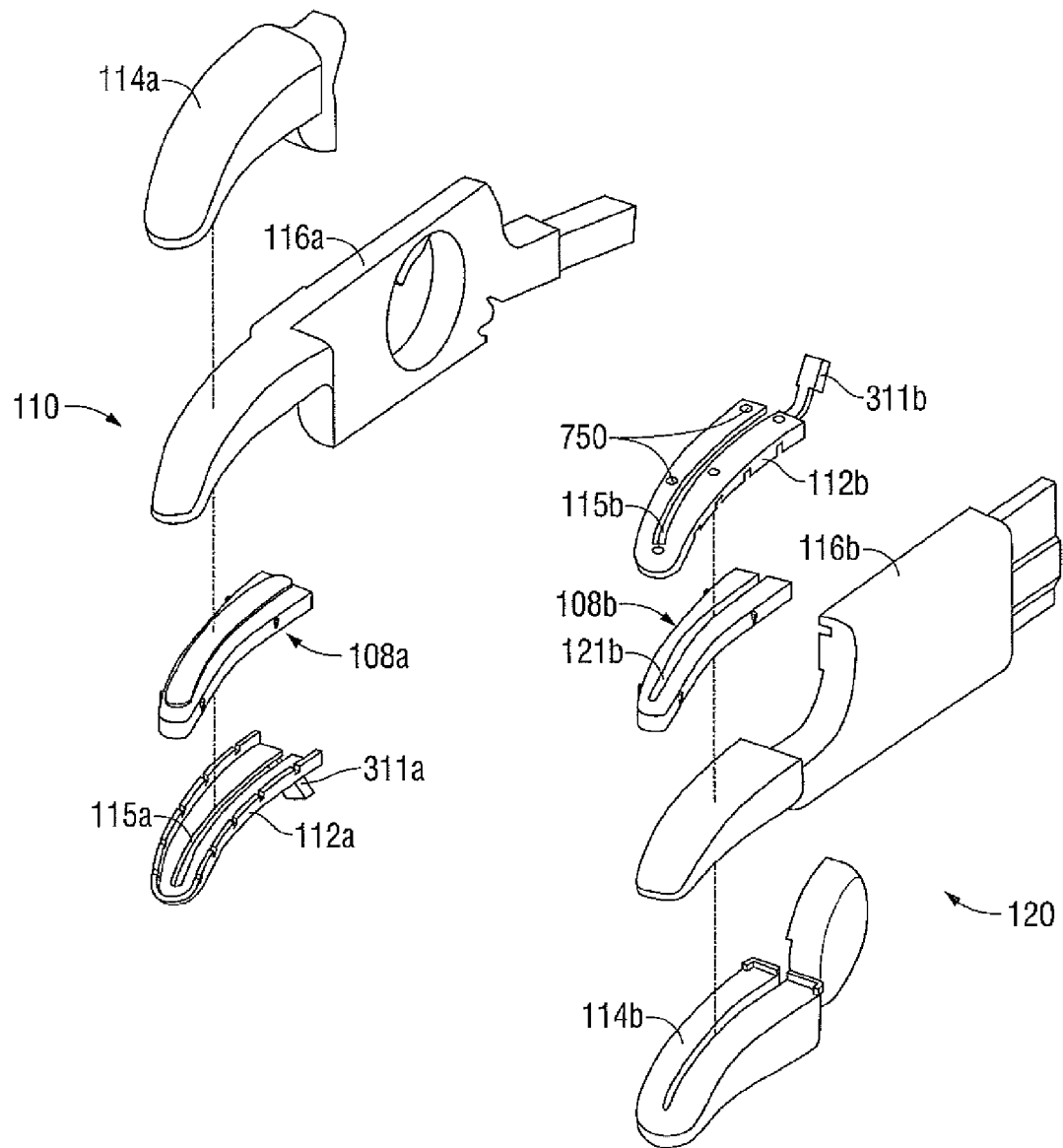
FIG. 3A is an exploded view of an end effector assembly of the forceps of FIG. 1.
Figure 3B:
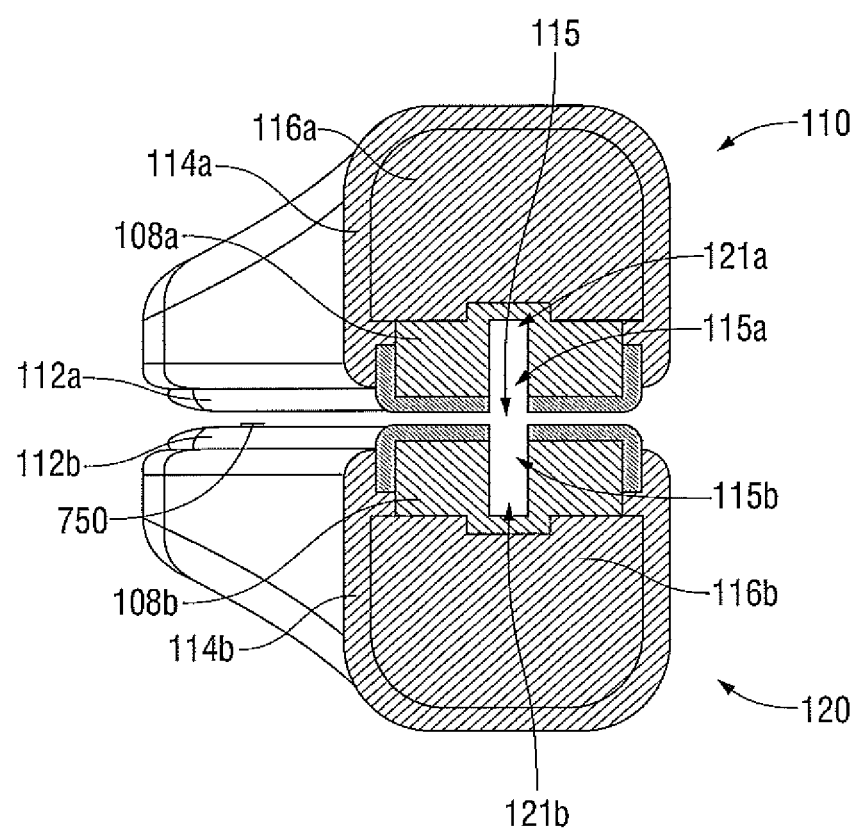
FIG. 3B is a cross-sectional view of the end effector assembly of the forceps of FIG. 1.

With reference to FIGS. 3A and 3B, jaw member 110 includes an outer housing 116a, first and second non-conductive plastic insulators 108a and 114a, and an electrically conductive sealing surface 112a. The first and second insulators 108a and 114a are overmolded about jaw housing 116a in a two-shot overmolding process. More specifically, the first insulator 108a is overmolded about jaw housing 116a to electrically insulate the jaw housing 116a from sealing surface 112a and the second insulator 114a is overmolded about jaw housing 116a to secure the electrically conductive sealing surface 112a thereto. This may be accomplished by stamping, by overmolding, by overmolding a stamped sealing surface, and/or by overmolding a metal injection molded sealing surface. The jaw members 110 and 120 are made from a conductive material. In some embodiments, the jaw members 110 and 120 are powder coated with an insulative coating to reduce stray current concentrations during sealing.

As best shown by the cross-sectional view of FIG. 3B, electrically conductive sealing surface 112a of jaw member 110 is pronounced from the jaw housing 116a and the second insulator 114a such that tissue is grasped by the opposing electrically conductive sealing surfaces 112a and 112b when jaw members 110 and 120 are in the closed position.

Likewise, jaw member 120 includes similar elements that correspond to jaw member 110 including: an outer housing 116b, first and second plastic insulators 108b and 114b, and an electrically conductive sealing surface 112b that is pronounced from the jaw housing 116b and second insulator 114b. As described above with respect to jaw member 110, the first insulator 108b electrically insulates the jaw housing 116b from the sealing surface 112b and the second insulator 114b secures the sealing surface 112b to the jaw housing 116b. Insulators 114a and 114b extend along the entire length of jaw members 110 and 120, respectively, to reduce alternate or stray current paths during sealing. In some embodiments, each of sealing surfaces 112a and 112b may include an outer peripheral edge that has a radius such that each insulator 114a and 114b meets the respective sealing surface 112a and 112b along an adjoining edge that is generally tangential to the radius and/or meets along the radius.

As shown in FIGS. 3A and 3B, at least one of the jaw members, e.g., jaw member 120, includes at least one stop member 750 disposed on the inner facing surfaces of the electrically conductive sealing surface 112b and/or 112a. Alternatively or in addition, the stop member(s) 750 may be disposed adjacent to the electrically conductive sealing surfaces 112a, 112b or proximate the pivot 65. The stop member(s) 750 facilitate gripping and manipulation of tissue and to define a gap between opposing jaw members 110 and 120 during sealing and cutting of tissue. In some embodiments, the stop member(s) 750 maintain a gap distance between opposing jaw members 110 and 120 within a range of about 0.001 inches (~0.03 millimeters) to about 0.006 inches (~0.015 millimeters).

As shown in FIG. 2, shaft 12b includes a beam 57 disposed therein and extending between handle 15 and jaw member 110. In some embodiments, the beam 57 is constructed of flexible steel to allow the user to generate additional sealing pressure on tissue grasped between the jaw members 110 and 120. More specifically, once end effector assembly 100 is closed about tissue, the shafts 12a and 12b may be squeezed toward each other to utilize the flexibility of the beam 57 to generate the necessary closure pressure between jaw members 110 and 120. In this scenario, the mechanical advantage realized by the compressive force associated with the beam 57 facilitates and assures consistent, uniform, and accurate closure pressure about tissue grasped between jaw members 110 and 120 (e.g., within a working pressure range of about 3 kg/cm$^2$ to about 16 kg/cm$^2$). By controlling the intensity, frequency, and duration of the electrosurgical energy applied to the tissue, the user can seal tissue. In some embodiments, the gap distance between opposing sealing surfaces 112a and 112b during sealing ranges from about 0.001 inches to about 0.005 inches.

In some embodiments, the sealing surfaces 112a and 112b are relatively flat to avoid current concentrations at sharp edges and to avoid arcing between high points. In addition, and due to the reaction force of the tissue when engaged, each of jaw members 110 and 120 may be manufactured to resist bending, e.g., tapered along its length to provide a constant pressure for a constant tissue thickness at parallel and the thicker proximal portion of the jaw members 110 and 120 will resist bending due to the reaction force of the tissue.

As shown in FIGS. 3A, 3B, 4B, and 4C, at least one of jaw members 110 and 120 includes a knife channel 115a and/or 115b, respectively, disposed therebetween that is configured to allow reciprocation of a knife 85 therethrough. In the illustrated embodiment, a complete knife channel 115 is formed when two opposing channel halves 115a and 115b associated with respective jaw members 110 and 120 come together upon grasping of the tissue. Each plastic insulator 108a and 108b includes a trough 121a and 121b, respectively, that aligns in vertical registration with an opposing knife channel half 115a and 115b, respectively, such that knife 85 does not contact or cut through plastic insulators 108a and 108b upon reciprocation through knife channel 115. In some embodiments, the width of knife channels 115a and 115b and their respective troughs 121a and 121b may be equal along an entire length thereof.

Figure 4A:
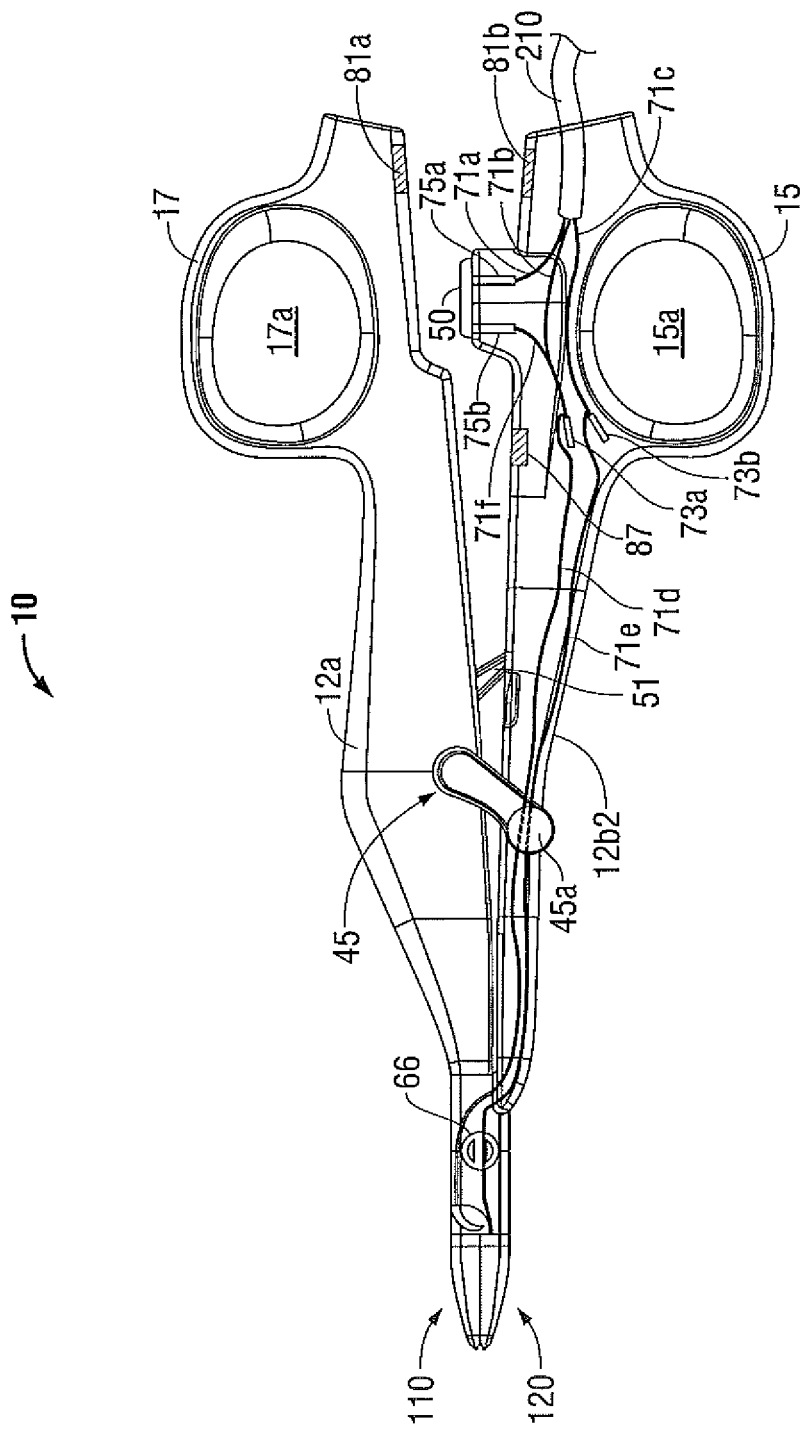
FIG. 4A is a side view of the forceps of FIG. 1 with parts partially removed to show the electrical connection between a switch and the end effector assembly.

As best shown in FIG. 4A, the interior of cable 210 houses leads 71a, 71b and 71c. Leads 71a, 71b, and 71c extend from the plug 200 through cable 210 and exit the distal end of the cable 210 within the proximal connector 19 of shaft 12b. More specifically, lead 71a is interconnected between prong 202b and a first terminal 75a of the switch 50. Lead 71b is interconnected between prong 202c and a solder sleeve 73a which, in turn, connects lead 71b to an RF lead 71d and to a second terminal 75b of the switch 50 via a connector lead 71f. RF lead 71d carries a first electrical potential of electrosurgical energy from lead 71b to sealing surface 112a. Lead 71c is interconnected between prong 202a and a solder sleeve 73b which, in turn, connects lead 71c to an RF lead 71e. RF lead 71e carries a second electrical potential of electrosurgical energy from lead 71c to sealing surface 112b.

Figure 4B:
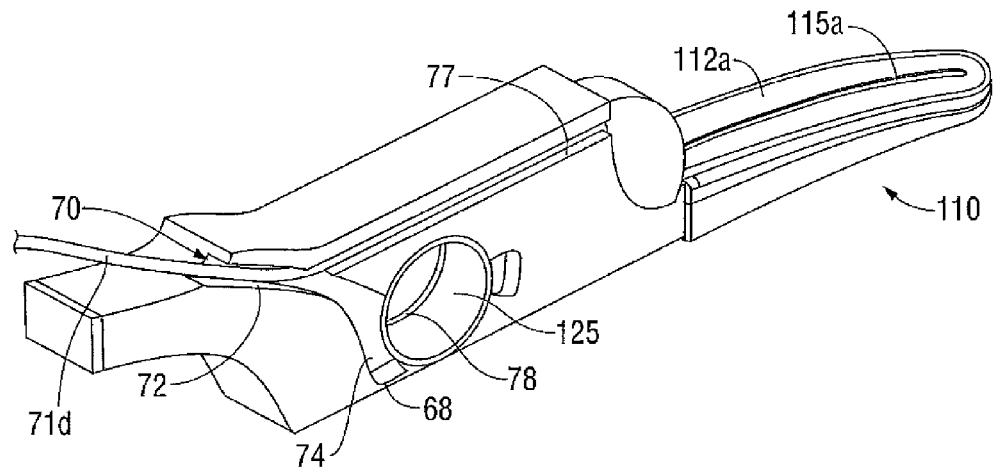
FIG. 4B is a left, perspective view of a jaw member of the end effector assembly of FIG. 1.

With reference to FIG. 4B, a lead channel 77 is defined in the proximal end of jaw member 110 to provide a pathway for lead 71d to connect to a junction 311a (FIG. 3A) extending from a proximal end of sealing surface 112a. A proximal end of lead channel 77 opens into a raceway 70 that includes a generally elongated configuration with a narrowed proximal end 72 and a broadened distal end 74 that defines an arcuate sidewall 68. Lead 71d is routed to follow a path through the proximal end 72 of raceway 70 and, further, through lead channel 77 for connection to junction 311a.

Figure 4C:
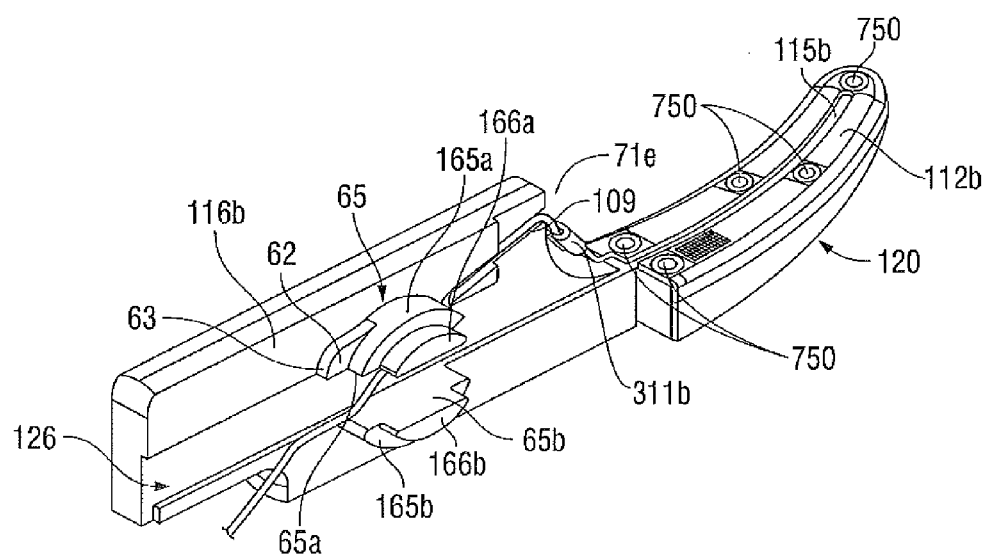
FIG. 4C is a left, perspective view of a jaw member of the end effector assembly of FIG. 1.
Figure 5A:
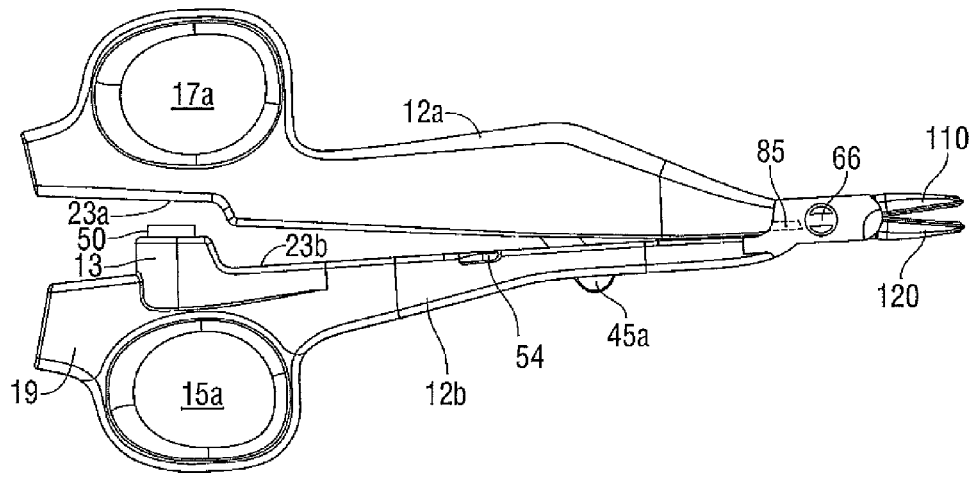
FIGS. 5A-5C are side views of the forceps of FIG. 1 illustrating actuation thereof between open and closed positions.
Figure 5B:
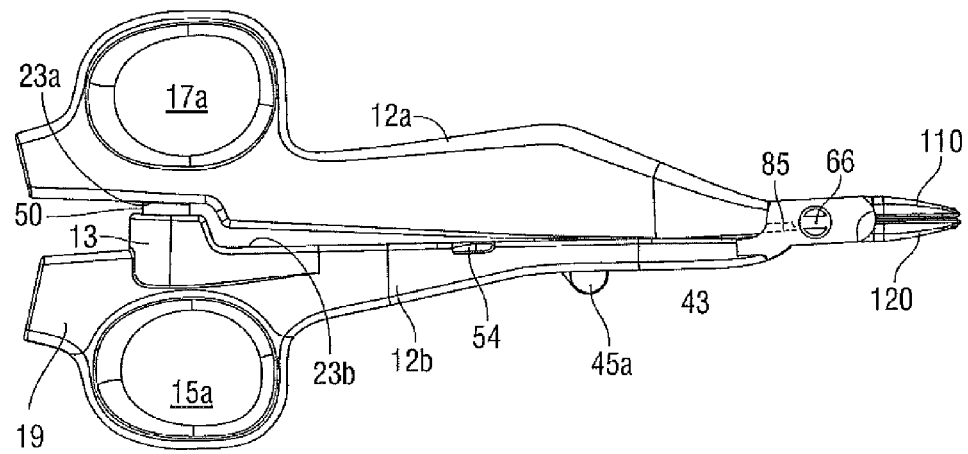
Figure 5C:
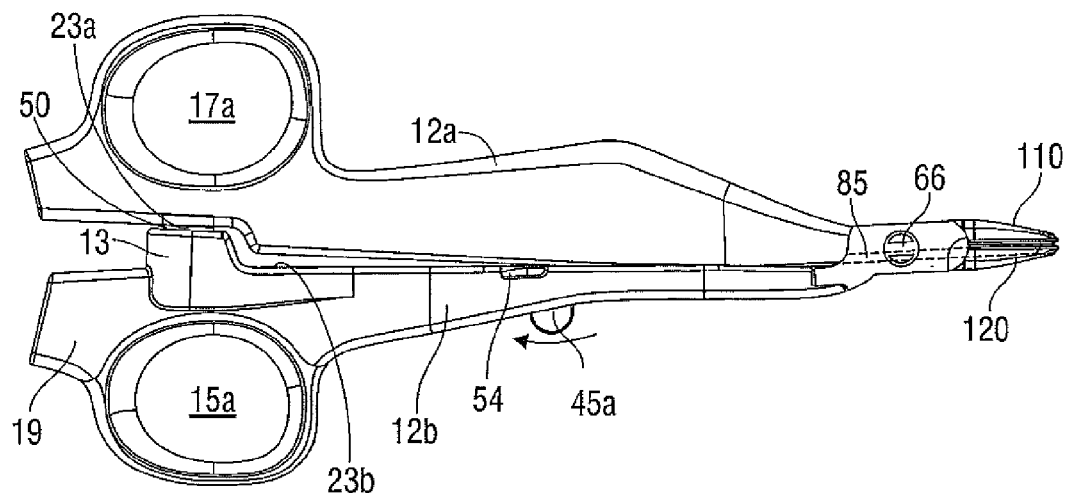
Figure 6:
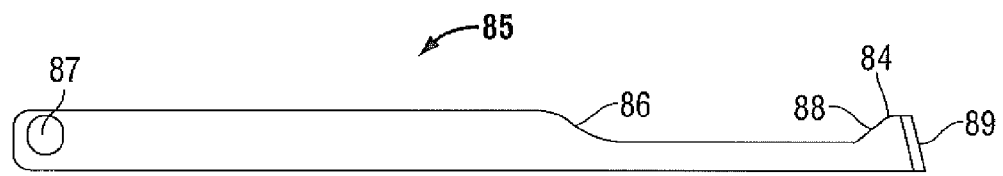
FIG. 6 is a side view of a knife for use with the forceps of FIG. 1 according to one embodiment of the present disclosure.

With reference to FIG. 4C, pivot halves 65a and 65b are disposed on opposing sides of channel 126 to facilitate translation of the knife 85 therethrough (FIGS. 5A-5C). Pivot halves 65a and 65b are disposed in a split spherical configuration and each include a respective base portion 165a and 165b that support an extension portion 166a and 166b thereon, respectively. Extension portions 166a and 166b are configured to engage correspondingly-dimensioned apertures 67a and 67b, respectively, disposed through pivot plate 66 to pivotably secure jaw member 110 to jaw member 120. A lead channel 109 is defined in the proximal end of jaw member 120 to provide a pathway for lead 71e to connect to a junction 311b extending from a proximal end of sealing surface 112b. Lead 71e is routed to follow a path through raceway 70 and, further between opposing pivot halves 65a and 65b and through lead channel 109 for connection to junction 311b.

With reference to FIGS. 5A-5C, as the user applies closure pressure on shafts 12a and 12b to depress switch 50 (FIG. 5B), a first threshold is met corresponding to the closure force applied to switch 50 as a function of displacement of switch 50 that causes switch 50 to generate a first tactile response that corresponds to a complete grasping of tissue disposed between jaw members 110 and 120. Following the first tactile response, as the user applies additional closure pressure on shafts 12a and 12b (FIG. 5C), a second threshold is met corresponding the closure force applied to switch 50 as a function of displacement of switch 50 that causes the switch 50 to generate a second tactile response that corresponds to a signal being generated to the electrosurgical generator to supply electrosurgical energy to the sealing surfaces 112a and 112b. More specifically, the second tactile response indicates closing of a normally open circuit between switch terminals 75a and 75b and, in turn, establishment of an electrical connection between leads 71a and 71b. As a result of the electrical connection between leads 71a and 71b, the electrosurgical generator senses a voltage drop between prongs 202b and 202c and, in response thereto, supplies electrosurgical energy to sealing surfaces 112a and 112b via leads 71d and 71e, respectively.

In one embodiment, the first tactile response indicates to the user that the maximum grasping pressure has been reached before end effector 100 is energized where the user is free to approximate, manipulate, and grasp tissue as needed. In this scenario, the second tactile response indicates to the user the electrosurgical activation of the end effector 100. The switch 50 may include a plurality of other tactile responses between the above discussed first and second tactile responses and/or subsequent to the second tactile response that correspond to particular functions of the forceps 10 such as, for example, operation of the knife 85 and/or the actuation assembly 40, operation of a safety lockout mechanism associated with the actuation assembly 40, as discussed in detail below.

As shown in FIG. 4A, forceps 10 may include a gauge or sensor element 87 disposed within one or both of shafts 12a, 12b such that the clamping or grasping forces being applied to target tissue by end effector 100 may be measured and/or detected. For example, in some embodiments, sensor element 87 may be a strain gauge 87 operably associated with one or both jaw members 110, 120. Sensor element 87 may be one or more Hall effect sensors or strain gauges such as, for example, metallic strain gauges, piezoresistive strain gauges, that may be disposed within one or both of shafts 12a and 12b and/or within one or both of jaw members 110 and 120 to detect tissue pressure. Metallic strain gauges operate on the principle that as the geometry (e.g., length, width, thickness, etc.) of the conductive material changes due to mechanical stress, the resistance of the conductive material changes as a function thereof. This change in resistance is utilized to detect strain or applied mechanical stress such as, for example, the mechanical stress applied to tissue by jaw members 110 and 120. Piezoresistive strain gauges operate based on the changing resistivity of a semiconductor due to the application of mechanical stress.

Hall effect sensors may be incorporated to determine the gap between jaw members 110 and 120 based on a detected relationship between the magnetic field strength between jaw members 110 and 120 and the distance between jaw members 110 and 120.

In some embodiments, one or more reed switches 81a, 81b may be incorporated within shafts 12a and 12b to determine the proximity thereof relative to one another, as shown in FIG. 4A. More specifically, the reed switch(es) may be comprised of a switch 81a disposed within one of the shafts (e.g., shaft 12a) and a magnetic element 81b (e.g., electromagnet, permanent magnet, coil, etc.) disposed within the opposing shaft (e.g., shaft 12a) such that upon approximation of shafts 12a and 12b, the reed switch 81a is activated or closed by the magnetic field of the magnetic element 81b and, likewise, as shafts 12a and 12b are moved away from each other, the lack of magnetic field operates to deactivate or open the reed switch 81a. In this manner, the proximity of shafts 12a and 12b and thus, jaw members 110 and 120, may be determined based on the reaction of the reed switch 81a to the magnetic element 81b.

Any of the above discussed sensors, switches, and/or strain gauge(s) may be incorporated within an electrical circuit such that the strain detected by the strain gauge changes the electrical signal through the circuit. With this purpose in mind, an electrical circuit between the strain gauge and the switch 50 and/or an electrosurgical generator (not shown) allows communication of information such as desired tissue pressure thereto. This information may be tied to the activation of switch 50 such that the switch is not activated until a desired and/or predetermined pressure on tissue grasped between jaw members 110 and 120 is achieved as detected by the strain gauge. Accordingly, the strain gauge may be disposed strategically on the forceps 10, e.g., on one or more of jaw members 110, 120, such that pressure applied to tissue grasped between jaw members 110 and 120 affects the strain gauge.

In use, forceps 10 may be calibrated such that particular tactile responses (e.g., the first tactile response) of switch 50 corresponds to a predetermined grasping pressure on tissue as determined through use of one or more of the above discussed sensors, switches, and/or strain gauge(s). The predetermined grasping pressure about tissue is within the range of about 3 kg/cm$^2$ to about 16 kg/cm$^2$ in one embodiment and, in another embodiment, about 7 kg/cm$^2$ to about 13 kg/cm$^2$. In some embodiments, switch 50 may generate multiple tactile responses, each of which corresponds to different predetermined grasping force. For a more detailed discussion of force sensing and/or measuring devices such as load cells, strain gauges, etc., reference is made to commonly-owned U.S. application Ser. No. 11/409,154, filed on Apr. 21, 2006.

As shown in FIGS. 2, 4B, and 4C, the pivot 65 connects through an aperture 125 defined through jaw member 120 and matingly engages a pivot plate 66 seated within a circumferential lip or flange 78 (FIG. 4B) defined around the periphery of aperture 125 such that the pivot 65 is rotatably movable within the aperture 125 to move jaw members 110 and 120 between open and closed positions.

In some embodiments, actuation of the knife 85 is associated with activation of the switch 50. For example, sensor 87 may be embodied as a position sensor configured to detect the position of knife 85 relative to jaw members 110 and 120 and/or relative to tissue held therebetween. Additionally or alternatively, sensor 87 may be configured to detect either of the first and second tactile responses of switch 50 and allow or prevent actuation of the knife 85 accordingly. For example, based on feedback from the sensor 87, any one or more inter-cooperating elements or lockout mechanisms associated with the actuating mechanism 40 may be energized or de-energized to allow or prevent actuation of the knife 85, as described in more detail below.

As shown in FIG. 7, knife 85 includes a step 86 that reduces the profile of the knife 85 toward a distal end thereof. The distal end of the knife 85 has a step 88 that increases the profile of the knife 85 toward a sharpened distal cutting edge 89. The knife 85 includes a chamfered portion 84 where the sharpened distal cutting edge 89 meets the step 88 to facilitate smooth retraction of knife 85 through the knife channel 15.

In some embodiments, the forceps 10 may include a safety lockout mechanism having a series of suitable inter-cooperating elements (e.g., anti-deployment link 47, trigger link 47) that work together to prevent unintentional firing of the knife 85 when the jaw members 110 and 120 are disposed in the open position. Generally, the anti-deployment link 47 mechanically cooperates with the trigger link 43 to prevent advancement of the knife 85 until the jaw members 110 and 120 are closed about tissue. One such safety lockout mechanism for use with forceps 10 is described in commonly-owned U.S. application Ser. No. 12/896,100 entitled "Blade Deployment Mechanisms for Surgical Forceps", filed on Oct. 1, 2010.

In some embodiments, any one or more of the inter-cooperating elements of the safety lockout mechanism (e.g., anti-deployment link 47) may be electrically interconnected to the switch 50 and include suitable electro-mechanical components (e.g., springs, rods, solenoids, etc.) configured to be energized via activation of the switch 50 (e.g., via any one of leads 71a, 71b, 71c, 71d, 71e) to mechanically manipulate the safety lockout mechanism. For example, upon electrical conduction through leads 71d and 71e to energize the end effector 100, the anti-deployment link 47 is energized to cause actuation thereof such that the safety lockout mechanism disengages to allow selective actuation of the knife 85. In this scenario, by way of example, selective actuation of the knife 85 may be prevented until switch 50 has been depressed to generate at least the first tactile response.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A bipolar electrosurgical instrument, comprising:
   first and second shafts each having a jaw member extending from a distal end thereof and a handle disposed at a proximal end thereof for effecting movement of the jaw members relative to one another about a pivot, the jaw members movable between a first position wherein the jaw members are disposed in spaced relation relative to one another and a second position wherein the jaw members cooperate for grasping tissue therebetween, each jaw member adapted to connect to a source of electrosurgical energy such that the jaw members are capable of selectively conducting energy through tissue held therebetween to effect a tissue seal;
   at least one of the jaw members including a knife channel defined along a length thereof, the knife channel configured to receive a cutting mechanism therethrough to cut tissue grasped between the jaw members;
   an actuator pivotably coupled to the first shaft such that rotation of the actuator selectively reciprocates the cutting mechanism through the knife channel;
   an anti-deployment link pivotably coupled to the first shaft and configured to engage the actuator within the first shaft to prevent distal translation of the cutting mechanism when the jaw members are in the first position; and
   a switch disposed on the first shaft and configured to be depressed relative to the first shaft to a first position and at least one subsequent position upon biasing engagement with the second shaft, wherein the first position of the switch generates information corresponding to a grasping pressure and the at least one subsequent position of the switch is configured to activate the source of electrosurgical energy.

2. The bipolar electrosurgical instrument according to claim 1, wherein the switch generates a first tactile response upon depression thereof to the first position and a subsequent tactile response upon depression thereof to the at least one subsequent position.

3. The bipolar electrosurgical instrument according to claim 1, wherein the grasping pressure is in the range of about 3 kg/cm² to about 16 kg/cm² measured by at least one strain gauge disposed within the bipolar electrosurgical instrument.

4. The bipolar electrosurgical instrument according to claim 1, wherein the grasping pressure is in the range of about 3 kg/cm² to about 16 kg/cm² determined by a sensed proximity of the first and second shafts relative to each other.

5. A bipolar electrosurgical instrument according to claim 1, further comprising first and second electrical leads bundled in a single cable that operatively couples to one of the first or second shafts.

6. The bipolar electrosurgical instrument according to claim 5, wherein at least one of the first or second electrical leads is disposed through the pivot and coupled to one of the first or second jaw members.

7. A bipolar electrosurgical instrument according to claim 1, wherein each of the jaw members includes an electrically conductive sealing surface and at least one of the jaw members includes at least one non-conductive stop member disposed on the electrically conductive sealing surface configured to control the distance between opposing electrically conductive sealing surfaces when the jaw members are disposed in the second position.

8. The bipolar electrosurgical instrument according to claim 1, wherein the grasping pressure is in the range of about 3 kg/cm² to about 16 kg/cm².

9. A bipolar electrosurgical instrument, comprising:
first and second shafts each having a jaw member extending from a distal end thereof and a handle disposed at a proximal end thereof for effecting movement of the jaw members relative to one another about a pivot, the jaw members movable between a first position wherein the jaw members are disposed in spaced relation relative to one another and a second position wherein the jaw members cooperate for grasping tissue therebetween, each jaw member adapted to connect to a source of electrosurgical energy such that the jaw members are capable of selectively conducting energy through tissue held therebetween to effect a tissue seal;
at least one of the jaw members including a knife channel defined along a length thereof, the knife channel configured to receive a cutting mechanism therethrough to cut tissue grasped between the jaw members;
an actuator pivotably coupled to the first shaft such that rotation of the actuator selectively reciprocates the cutting mechanism through the knife channel;
an anti-deployment link pivotably coupled to the first shaft and configured to engage the actuator within the first shaft to prevent distal translation of the cutting mechanism when the jaw members are in the first position; and
a switch disposed on the first shaft and configured to be depressed relative to the first shaft to at least two positions upon biasing engagement with the second shaft, the switch generating a first tactile response upon depression to a first position of the at least two positions of the switch and a subsequent tactile response upon depression to a second position of the at least two positions of the switch, wherein the first position of the switch generates information corresponding to a grasping pressure and the second position of the switch is configured to activate the source of electrosurgical energy.

10. The bipolar electrosurgical instrument according to claim 9, wherein the grasping pressure is in the range of about 3 kg/cm² to about 16 kg/cm².

* * * * *